United States Patent [19]

Cutmore

[11] Patent Number: 5,333,493
[45] Date of Patent: Aug. 2, 1994

[54] MOISTURE CONTENT BY MICROWAVE PHASE SHIFT AND MASS/AREA

[75] Inventor: Nicholas G. Cutmore, Woronora Heights, Australia

[73] Assignee: Commonwealth Scientific and Industrial Research Organisation, Australia

[21] Appl. No.: 834,573

[22] PCT Filed: Aug. 15, 1990

[86] PCT No.: PCT/AU90/00351

§ 371 Date: Feb. 13, 1992

§ 102(e) Date: Feb. 13, 1992

[87] PCT Pub. No.: WO91/02966

PCT Pub. Date: Mar. 7, 1991

[30] Foreign Application Priority Data

Aug. 15, 1989 [AU] Australia .................. PJ 5784

[51] Int. Cl.$^5$ ............. G01N 23/00; G01R 23/00; G01R 25/00
[52] U.S. Cl. ........................ 73/73; 324/640
[58] Field of Search ......... 324/637, 639, 640, 634; 73/73

[56] References Cited

U.S. PATENT DOCUMENTS

| | | |
|---|---|---|
| 3,851,244 | 11/1974 | Mounce . |
| 3,913,012 | 10/1975 | Kujath . |
| 4,193,027 | 3/1980 | Wyslouzil . |
| 4,233,559 | 11/1980 | Hoberg et al. ............ 324/639 |
| 4,297,874 | 11/1981 | Sasaki ...................... 73/73 |
| 4,361,801 | 11/1982 | Meyer et al. ............ 324/640 X |
| 4,475,080 | 10/1984 | Walker . |
| 4,492,915 | 1/1985 | Caspers ................... 324/637 X |
| 4,674,325 | 6/1987 | Kiyobe et al. ............ 73/159 |
| 4,675,595 | 6/1987 | Hane ........................ 324/640 |
| 4,727,311 | 2/1988 | Walker ..................... 324/640 |
| 4,788,853 | 12/1988 | Bell .......................... 73/73 |
| 4,789,820 | 12/1988 | Parrent, Jr. et al. ......... 73/73 X |
| 5,086,279 | 2/1992 | Wochnowski et al. ...... 324/637 |
| 5,177,444 | 1/1993 | Cutmore .................... 324/637 |

FOREIGN PATENT DOCUMENTS

| | | |
|---|---|---|
| 6703386 | 12/1986 | Australia . |
| 3407819 | 6/1985 | Fed. Rep. of Germany . |
| 59-197842 | 11/1984 | Japan . |
| 238959 | 2/1990 | Japan . |
| 1312457 | 12/1985 | U.S.S.R. . |
| 1376747 | 12/1974 | United Kingdom . |
| 2122741 | 1/1984 | United Kingdom . |
| 2182149 | 5/1987 | United Kingdom . |
| 9102966 | 3/1991 | World Int. Prop. O. ......... 324/640 |

OTHER PUBLICATIONS

Klein, "Microwave Moisture Determination of Coal-A Comparison of Attenuation and Phase Measurement", 10th European Microwave Conference, Sep. 1980, pp. 526-530.

Hoer, "Using Six-Port and Eight-Port Junctions to Measure Active and Passive Circuit Parameters", National Bureau of Standards, Sep. 1975, pp. iii-22.

Tiuri et al, "Microwave Instrument for Accurate Moisture and Density Measurement of Timber", Journal of Microwave Power, vol. 15, No. 4, 1980, pp. 251-254.

Primary Examiner—William A. Cuchlinski, Jr.
Assistant Examiner—W. Morris Worth
Attorney, Agent, or Firm—Leydig Voit & Mayer

[57] ABSTRACT

Apparatus and methods for the determination of moisture content of a sample carried on a conveyor belt. Microwave signals at a number of discrete frequencies within a range are transmitted through the sample and the phase shift of the received signals is averaged and combined with measurement of attenuation or mass per unit area to provide a measure of moisture content of the sample. The invention is applicable to measurement of moisture content of crushed coking and steaming coals.

20 Claims, 5 Drawing Sheets

MOISTURE CONTENT BY MICROWAVE PHASE SHIFT AND MASS/AREA

TECHNICAL FIELD

This invention relates to the determination of the moisture content of a sample from the phase-shift and attenuation of a transmitted microwave signal.

BACKGROUND ART

The measurement of moisture content is important in many industrial processes. The conventional methods of moisture measurement, based on oven-drying of a sample taken from the process stream, are frequently not rapid enough for quality control purposes and rely on the small sample analysed being representative of the total stream. Consequently, there is a requirement for on-line analysis techniques that provide a continuous analysis of the process stream.

One important example is in the on-line measurement of moisture in coal carried on a conveyor belt. In recent years there has been a growing interest in measuring and controlling the moisture content of coking and steaming coals. Moisture in these coals has increased mainly because of the increased proportion of fine coal in preparation plants as a result of modern mining methods and because greater emphasis is placed on fine coal recovery for economic reasons. Lower product coal moisture results in lower transport costs, energy savings when the coal is utilised and reduced handling difficulties.

A number of techniques have been investigated for the on-line determination of moisture in coal. These include capacitance measurement, microwave transmission, fast neutron and gamma-ray transmission, infrared reflectance and nuclear magnetic resonance.

Moisture measurement by microwave techniques is based either on the high real or imaginary part of the complex dielectric constant of water compared to the dielectric properties of the majority of dry materials. The complex dielectric constant ($\epsilon = \epsilon' - j\epsilon''$) is a function of the dielectric constant ($\epsilon'$) and the loss factor ($\epsilon''$) of a material, and for coal is not only influenced by the moisture content, but also other material properties such as bulk density, ash content and coal rank. The parameter most frequently used is a measurement of the attenuation or power loss of a transmitted beam of microwaves at a frequency in the range of 2-10 GHz, and for on-belt measurement of moisture in coal, a measurement of bulk density and/or coal layer thickness is also required.

A measurement of microwave attenuation has been widely used for the determination of moisture content in a range of materials. However, the attenuation measurement is very dependent on the sample thickness and sample position relative to the microwave source, and therefore use of the technique in on-line measurement applications has relied on presentation of a constant thickness layer of material to the gauge. This has been achieved using devices such as a levelling plough or a recirculating levelling conveyor that level the top surface of material carried on a conveyor belt. A disadvantage of these techniques is that contacting devices of this type may cause blockages in the flow of material. An alternative technique is to perform measurements on a sample by-line where sample presentation can be carefully controlled, however, this is more costly and the frequency of the analysis is determined by the rate of sampling.

A number of attempts have been made to modify the attenuation measurement technique to improve its accuracy for the determination of moisture content. These have involved an improved design of microwave apparatus to minimise interferences from reflection at the antennae, the use of reference signals to overcome problems with equipment drifts and the use of lens corrected antennae to improve signal directivity. However, the predominant error in the measurement of attenuation results from amplitude modulation of the transmitted signal by signals reflected from the sample/air interfaces. One proposed method of reducing the error resulting from such amplitude modulation is to measure the attenuation at 50-100 frequencies in a 0.5-1 octave frequency band and correlate the mean value with moisture content. This technique is reported to reduce the influence of variation in sample thickness and position on the attenuation measurement.

A measurement of microwave phase shift has also been investigated for the determination of moisture. In the on-line measurement of moisture by this technique the measured phase shift or attenuation are normalized to the sample mass per unit area determined from a gamma-ray transmission measurement.

A combined measurement of phase shift and attenuation has also been proposed to determine moisture independent of variations in the sample density. In this technique the moisture content is determined from the difference in the attenuation at two measurement frequencies and a measurement of phase shift compensates for density variation. However, for on-line measurement either a constant thickness sample or a measurement of sample thickness is required.

DISCLOSURE OF THE INVENTION

It is an object of this invention to provide a method and apparatus for the determination of the moisture content of a sample of varying thickness on a conveyor belt which will ameliorate some of the above disadvantages.

Accordingly, in one aspect the present invention consists in an apparatus for the determination of the moisture content of a sample of varying thickness on a conveyor belt, said apparatus comprising means to sequentially generate microwave signals at a plurality of discrete frequencies selected to compensate for frequency dependent cyclic variation in propagation characteristics within said sample; a first antenna located below said conveyor belt to direct said microwave signals through the sample; a second antenna disposed above said belt to receive the microwave signals transmitted through the sample; means to provide a measure of the phase shifts of the respective received signals with respect to the transmitted signals at each of said discrete frequencies; means to provide a measure of mass per unit area of the sample; and means to generate a measure of moisture content of the sample from said phase shifts and mass per unit area.

In a second aspect this invention consists in a method for the determination of the moisture content of a sample of varying thickness on a conveyor belt, said method comprising the step of sequentially transmitting through said sample microwave signals at a plurality of discrete frequencies selected to compensate for frequency dependent cyclic variation in propagation characteristics within said sample; a means in determining the phase shifts of the respective received signals with respect to the transmitted signals at each of said discrete frequencies; and determining the moisture content of the sample from said phase shifts and a measurement of mass per unit area.

Preferably the range of transmitted frequencies is within the range of 2 to 4 GHZ. Preferably, also, the number of discrete frequencies is greater than ten.

The antenna can be of any suitable kind, for example horns or dielectric rods. In the case of horn antennae the horns can be filled with the impedance matching material. In this case also, the horn is preferably positioned at a distance from the sample which is less than the wavelength of the microwave signal.

The plurality of discrete frequencies preferably comprises a range and the range encompasses substantially one period of the frequency dependent cyclic variation in propagation characteristics within the sample. Preferably also, the discrete frequencies are equally spaced within the range and the propagation characteristics are averaged to produce a representative value.

Variation in the mass per unit area of the material is compensated for using a combined measurement of phase shift and attenuation, or a separate determination of mass per unit area combined with phase shift. If the density of the material analysed is approximately constant then a measurement of thickness, determined by any suitable technique, for example, ultrasonic ranging, may be substituted for a measurement of mass per unit area. The preferred technique for on-line determination of moisture content utilises a measurement of microwave phase shift and sample mass per unit area.

The propagation of an electromagnetic wave (EM) in a dielectric medium is described by Maxwell's equations, and the complex amplitude given by $$E(1) = E_o \exp(-\gamma 1) \quad (1)$$

where $1$ is the distance travelled by the EM wave in the dielectric medium from some reference point where its amplitude was $E_o$, and $\gamma$ is the propagation constant of the wave given by $$\gamma = \alpha + j\beta \quad (2)$$

where $\alpha$ and $\beta$ are the attenuation and phase constants respectively. For a non-magnetic dielectric medium in free space $\alpha$ and $\beta$ are given by $$\alpha = \frac{2\pi}{\lambda_0} \left[ \frac{\epsilon'}{2\epsilon_0} [(1 + (\epsilon''/\epsilon')^2)^{\frac{1}{2}} - 1] \right]^{\frac{1}{2}} \quad (3)$$

$$\beta = \frac{2\pi}{\lambda_0} \left[ \frac{\epsilon'}{2\epsilon_0} [(1 + (\epsilon''/\epsilon')^2)^{\frac{1}{2}} + 1] \right]^{\frac{1}{2}} \quad (4)$$

where $\epsilon_o$ is permittivity of free space, $\lambda_o$ the wavelength in free space, $\epsilon'$ the dielectric constant of the medium and $\epsilon''$ the loss factor of the medium.

The attenuation constant $\alpha$ represents the attenuation of the EM wave (in nepers per meter) and the phase constant $\beta$ represents the phase shift of the EM wave (in radians per meter).

From equations (3) and (4), it can be seen that the attenuation and phase shift of an EM wave in a dielectric is a function of the complex permittivity of the medium, $$\epsilon^* = \epsilon' - j\epsilon'' \quad (5)$$

For a multicomponent dielectric medium the complex permittivity may be approximated by $$\epsilon^*_{medium} = \left( \sum_i v_i \sqrt{\epsilon^*_i} \right)^2 \quad (6)$$

where $v_i$ and $\epsilon^*_i$ are the volume fraction and complex permittivity of the $i^{th}$ component respectively.

Figure 1:
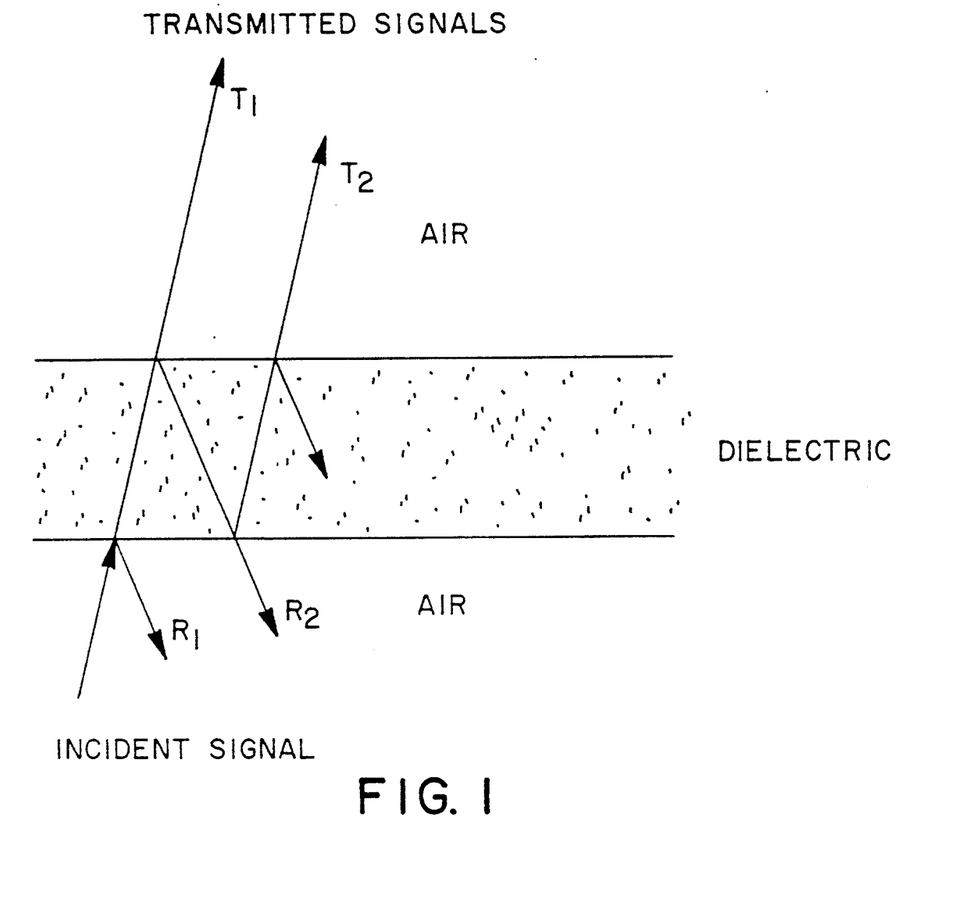
FIG. 1 is a schematic diagram showing transmitted and reflected EM waves generated on transmission of a microwave signal through a dielectric medium in air.

When a plane EM wave is incident upon a dielectric interface, part of it is reflected and part transmitted as illustrated in FIG. 1. For a non-magnetic dielectric in air the reflection coefficient, R, and transmission coefficient, T, are given by $$R = \frac{E_R}{E_0} = \frac{1 - \sqrt{\epsilon^*/\epsilon_0}}{1 + \sqrt{\epsilon^*/\epsilon_0}} \quad (7)$$

$$T = \frac{E_T}{E_0} = 1 + R \quad (8)$$

where $E_o$, $E_R$ and $E_T$ are the incident, reflected and transmitted electric field vectors.

The measured transmission coefficient may be expressed as $$T = 10^{-A/10} \exp\left( \frac{j \cdot 2\pi \cdot \theta}{360} \right) \quad (9)$$

where A is the measured attenuation in dB, and $\theta$ the measured phase shift in degrees. The actual phase shift due to the sample, $\phi$ is not determined in this measurement but is given by $$\phi = n.360 + \theta \quad (10)$$

where n is an integer.

Figure 2:
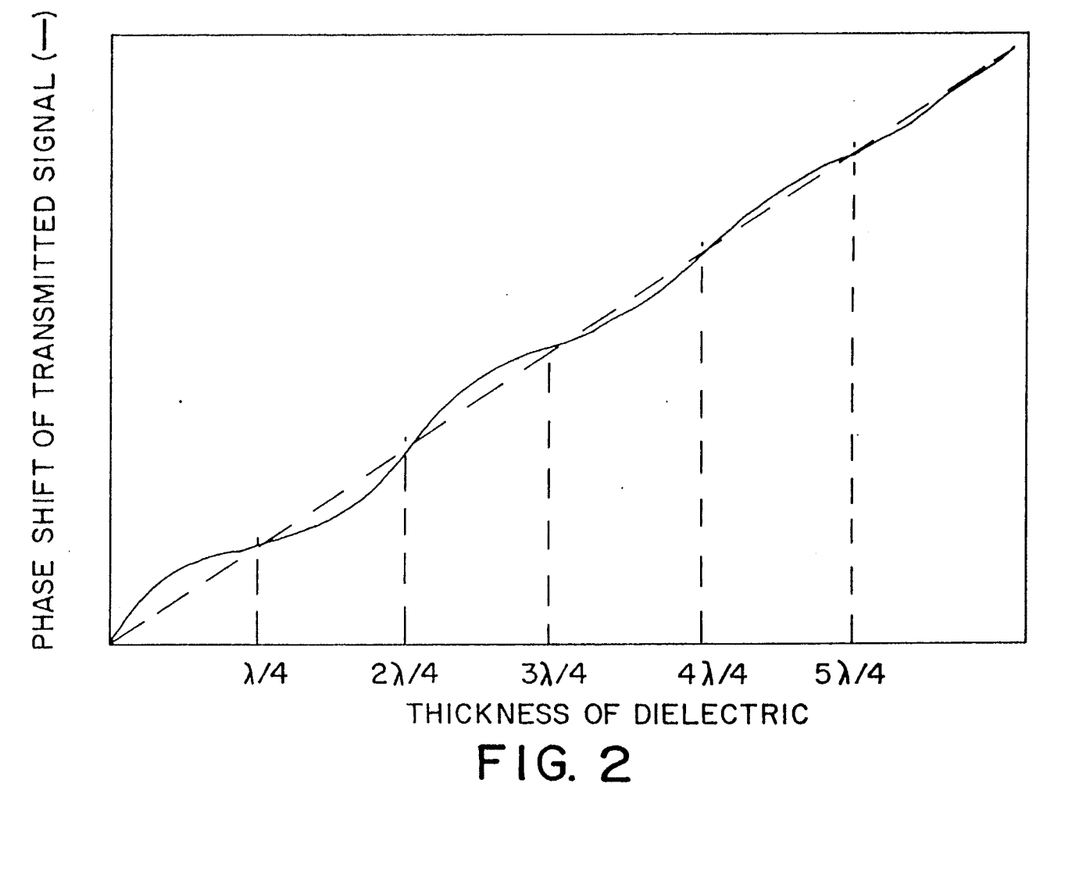
FIG. 2 is a schematic diagram showing the variation in the magnitude of the phase shift of a signal transmitted through a lossy dielectric, as a function of dielectric path length.
Figure 3:
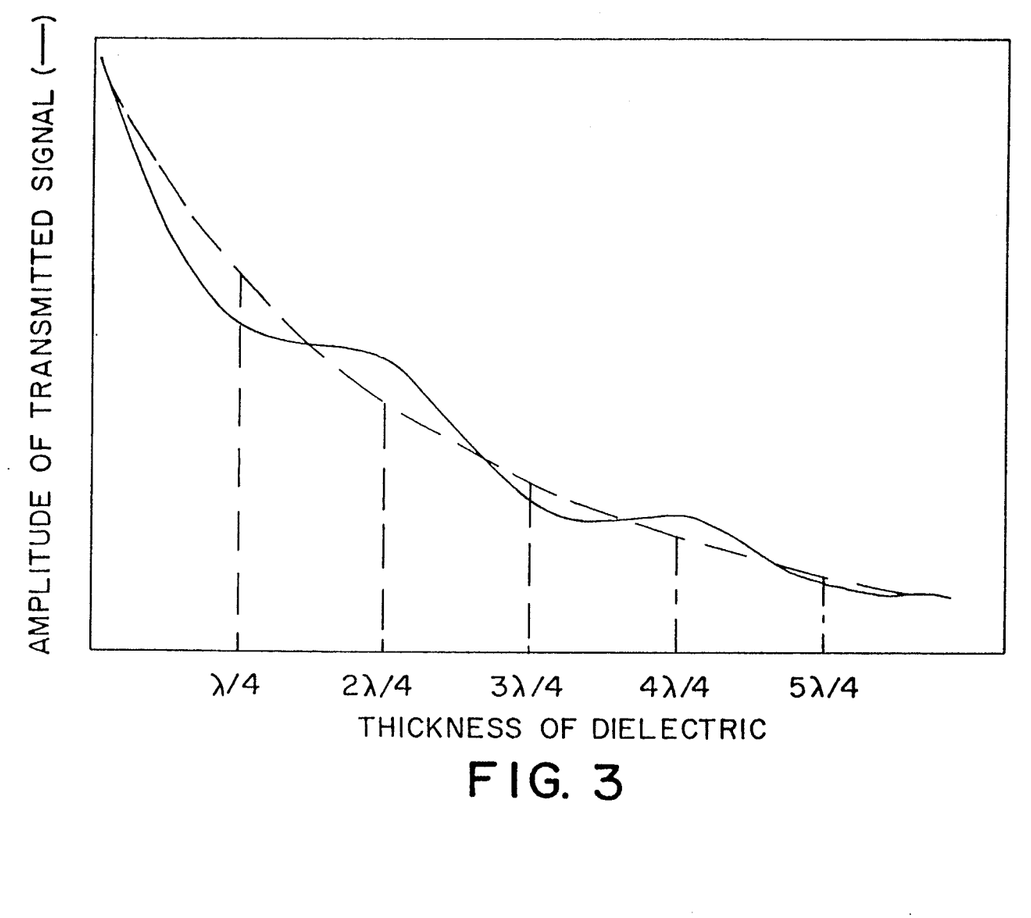
FIG. 3 is a schematic diagram showing the variation in the magnitude of the amplitude of a signal transmitted through a lossy dielectric, as a function of dielectric path length.

When an EM wave is incident upon a dielectric slab (FIG. 1), reflection at the sample-air interface results in multiple reflections within the dielectric slab. Consequently, the measured transmitted and reflected EM waves, at normal incidence, are found from $$T = \sum_i T_i = \sum_i a_i e^{j\phi_i} \quad (11)$$

$$R = \sum_i R_i = \sum_i b_i e^{j\theta_i} \quad (12)$$

where $T_i$ and $R_i$ are the component transmitted and reflected EM waves due to multiple reflections. For a lossy dielectric slab, $a_i << a_{i+1}$ and $b_i << b_{i+1}$, and T and R may be approximated from the sum of only the first two or three component signals. The effect of the change in the thickness of the dielectric on the measured phase shift and amplitude of T is shown in FIGS. 2 and 3 respectively. Both phase shift and amplitude vary in magnitude with a periodicity corresponding to an effective $\lambda/4$ change in the EM wave path length in the dielectric. The phase shift and amplitude of the reflected signal R, are found to also vary in a similar manner. That is, the propagation characteristics exhibit a frequency dependent cyclic variation. For a lossy dielectric, the magnitude of the variation in the phase shift and amplitude of the transmitted or reflected signals decreases with increasing sample thickness.

According to a preferred form of this invention a microwave signal is directed through a sample, using suitable transmitting and receiving antennae and the attenuation and phase shift of the signal due to the sample are measured. These are normally calculated as the difference between the attenuation and phase shift determined with the sample and with air. From equations (3) and (4) it can be seen that the phase shift and attenuation of the signal are functions of the effective complex permittivity $\epsilon^*$ of the sample, given by equation (6). The dielectric constant and loss factor of water at microwave frequencies are large compared to those for most other con, non materials, and therefore the phase shift and attenuation are strong functions of the moisture content of the sample.

It is known that in the measurement of moisture content of a sample by microwave transmission the phase shift is determined mainly by the effective dielectric constant of the material and is therefore independent of variations in the effective loss factor (caused by variations in material properties such as salt content or elemental composition) that significantly influence attenuation. In one form this invention seeks to remove the significant error in the measurement of phase shift, or attenuation, resulting from modulation of the transmitted signal by signals reflected from the sample/air interfaces. This is particularly significant in many on-line measurement applications where there is a variation in sample density or thickness, as this has the effect of varying the effective path length of the transmitted and reflected signals in the sample and, consequently the degree of amplitude modulation of the transmitted signal.

The component of the microwave signal reflected at each sample-air interface is determined by the difference in the refractive indices of the sample and air and the angle of incidence, and for non-conducting non-magnetic materials is effectively determined by the difference in the relative dielectric constants. According to this invention improving measurement accuracy includes the use of a matching dielectric medium between the microwave transmitting antenna and the sample to minimise secondary reflections of the microwave signal within the sample. If a horn antenna is used as the transmitter, this may be achieved by filling the horn with a dielectric that has a similar dielectric constant to the sample, and positioning the horn such that the horn to sample distance is significantly less than the wavelength of the microwave signal. As the effective dielectric constant of the sample varies proportionately with sample density and moisture content, perfect dielectric matching is not possible, however, dielectric matching to the mean effective dielectric constant of the sample is sufficient to obtain a significant improvement in measurement accuracy.

Phase shift and attenuation are determined from measurements at a range of frequencies, and the frequency range and number of measurements are selected to further minimise measurement error due to interference of transmitted and reflected signals. The periodicity in the interference of these signals corresponds to a $\lambda/4$ path length difference between them, and the range of sample thickness or density variation for this to occur is determined by the measurement frequency and sample effective dielectric constant. The same periodicity may be obtained at constant sample thickness for an equivalent variation $\Delta f$ of the measurement frequency. Determination of the moisture content from measurement of phase shift or attenuation over a frequency range $\Delta f$ (or $n\Delta f$ where n is an integer) is less affected by variation in sample thickness or density than measurement at a single frequency and a more accurate measurement of moisture is possible.

Figure 4:
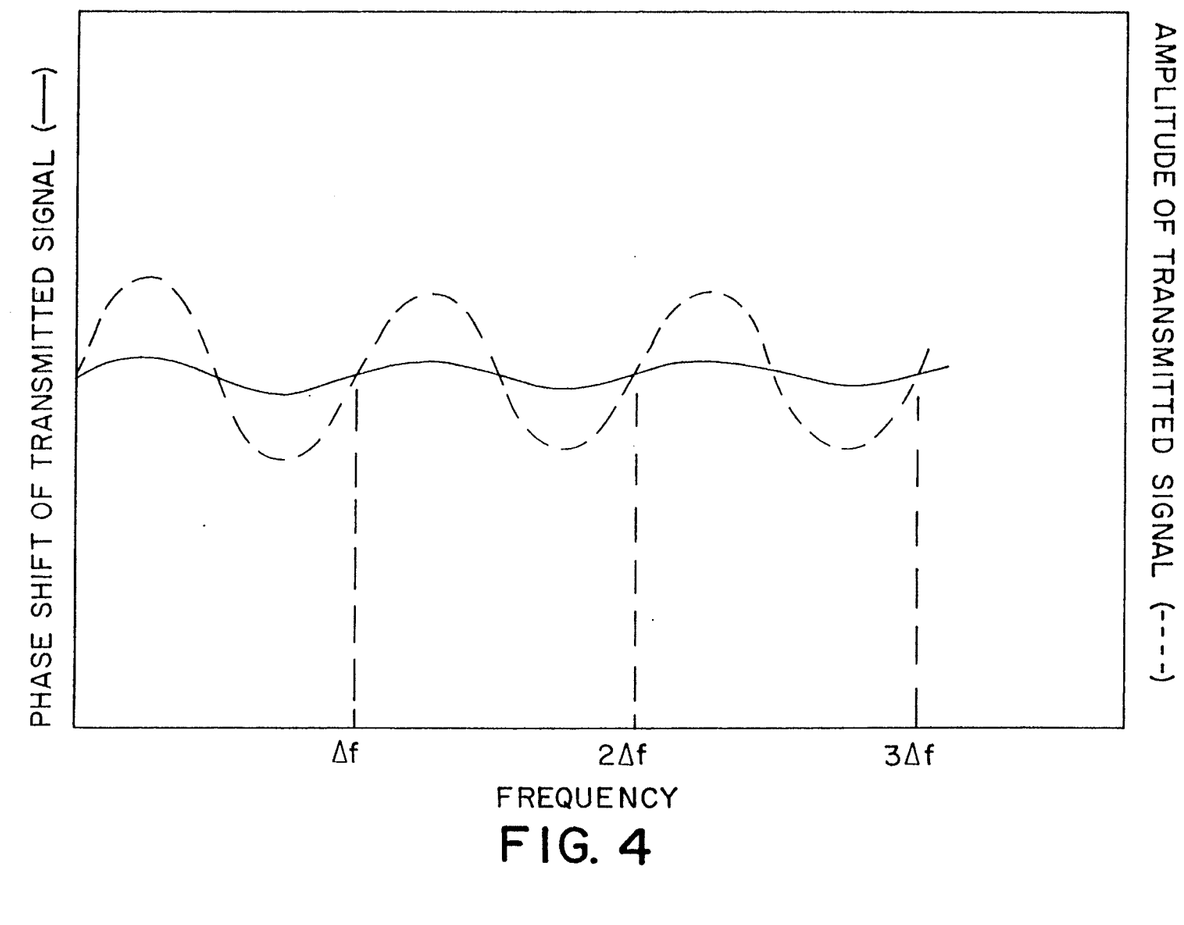
FIG. 4 is a schematic diagram showing the variation in the magnitude of the phase shift and amplitude of a signal transmitted through a constant thickness lossy dielectric as a function of frequency.

For example, in FIG. 2 the variation in the phase shift is repeated at $2(\lambda/4)$ intervals in the dielectric path length. The equivalent thickness of dielectric for this to occur is determined by the effective dielectric constant (Equation (6)) of the dielectric and the microwave frequency (f), and is given by, $$\lambda/2 = C/2f\sqrt{\epsilon^*_{medium}} \qquad (13)$$

where C is the velocity of light. For a dielectric of constant thickness the same periodicity in the measured phase shift will occur when the frequency is varied from $f_1$ to $f_2$, ($\Delta f = f_2 - f_1$), such that the dielectric path length is $(n\lambda)$ and $$\left( n\lambda_2 + \frac{\lambda_2}{2} \right)$$

respectively, (where $n = 1,2,3 ...$ ). However, in this instance only a single cycle of amplitude variation occurs as shown in FIG. 4. The transmitted signal amplitude varies in a similar manner, as shown in FIG. 4.

The error in the measurement of phase shift or attenuation can be significantly reduced by determining either parameter from the average of multiple measurements within the frequency range $f_1$ to $f_2$. Preferably, measurements at 10 or more frequencies, between $f_1$ and $f_2$, are made. However, a lesser number of measurements can be used if a lower measurement accuracy can be tolerated. The frequency may be varied over a wider range $n\Delta f$ (where, $n=1,2,3 ...$ ), however, this does not further improve measurement accuracy and has the disadvantage of requiring a wider bandwidth microwave oscillator.

BRIEF DESCRIPTION OF THE DRAWINGS

Some embodiments of this invention will now be described, by way of example only, with reference to the accompanying drawings in which.

MODES FOR CARRYING OUT THE INVENTION

Figure 5:
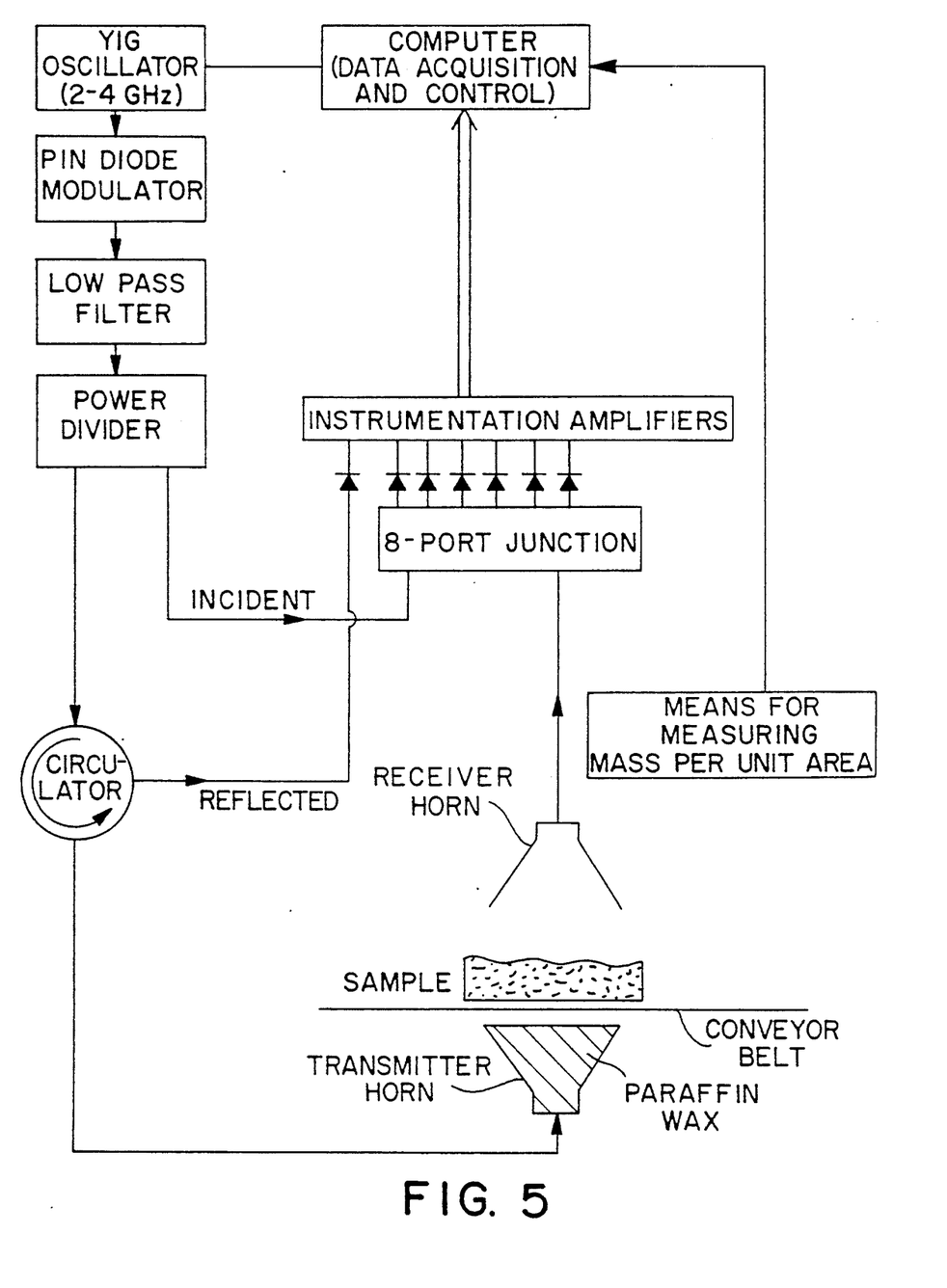
FIG. 5 is a schematic diagram of an apparatus for determination of moisture content of a sample from phase shift and attenuation of a transmitted microwave signal according to this invention.

Referring to FIG. 5, the apparatus according to this invention includes a yttrium-iron-garnet (YIG) oscillator as a microwave source. The oscillator is voltage tuneable over the frequency range 2-4 GHz at an output power level of approximately 30 mW. The oscillator output is amplitude modulated by a switchable pin diode attenuator at a frequency of approximately 1 khZ, and filtered by a low pass filter (with a 0-4 GHz passband) to reduce the power level of unwanted harmonics produced by the oscillator. After passing through a power divider, the microwave signal is coupled, via a circulator, to a horn antenna for transmission through a sample positioned on a conveyor belt immediately above the transmitter. The receiver is a horn antenna positioned 300-500 mm above the transmitter. Dielectric matching of the transmitter horn and sample is achieved by filling the horn with paraffin wax which has a dielectric constant of approximately 1.5 and negligible dielectric loss at 3 GHz.

The relative power level and phase difference of the incident and transmitted signals are determined using an 8-port junction that functions as a vector voltmeter in the substantially known manner. The reflected power at the transmitter horn is monitored at the return port of the circulator using a diode detector (not shown). The output voltage of the diode detector is fed to a.c. coupled instrumentation amplifiers (not shown), each with an adjustable output gain of 30-1000, and the voltage measured with a data logger interfaced to an IBM-PC computer (not shown).

The effect of dielectric matching of the transmitter and sample was determined from preliminary measurements on a perspex sample. Perspex was used because it has a low relative dielectric constant and loss factor, 2.25 and 0.02 respectively at 3 GHz, for which the predicted improvement in measurement accuracy was within the limit of detection of the measurement technique, and the thickness could be accurately measured. Measurements were made for a 6-66 mm thickness sample, in 6 mm steps, using the apparatus of FIG. 5 with and without dielectric matching of the transmitter. Measurements of attenuation and phase shift were linearly correlated with sample thickness using least squares regression and the r.m.s. errors obtained from these correlations are presented in Table 1 below. The r.m.s. errors in Table 1 represent the total measurement error, and one component of this is the error due to interference of transmitted and reflected signals. For phase shift there is approximately a 3.6 times improvement in measurement error for multiple frequency measurements with a dielectric filled transmitter as compared to a single frequency measurement in air. Correspondingly for attenuation, the measurement error is reduced by a factor of approximately 3.1 times.

TABLE 1

R.m.s. errors for correlations of phase shift and attenuation versus thickness from measurements using the gauge in FIG. 1.

| Measurement Conditions | Measurement Frequency (GHz) | Perspex Thickness (mm) | R.m.s. Error Attenuation (dB) | R.m.s. Error Phase Shift (degrees) |
|---|---|---|---|---|
| In air | 3.3 | 6≠66 | 0.297 | 5.0 (6.1%)* |
| Dielectric filled transmitter | 3.3 | 6-66 | 0.243 | 3.6 (4.4%) |
| In air | 2.8-3.8 | 6-66 | 0.120 | 2.7 (3.3%)* |
| Dielectric filled transmitter | 2.8-3.8 | 6-66 | 0.096 | 1.4 (1.7%)* |

Mean % relative error = (R.m.s. error/Mean Phase Shift × 100%.

To compare phase shift and attenuation measurement techniques for the determination of moisture in coal, measurement were made on a range of total product coals (from NSW coal washeries) using the apparatus of FIG. 5. Details of the coal samples used in these measurements are given in Table 2.

TABLE 2

Ash and particle size distributions of coal samples used in laboratory measurements on the prototype microwave moisture guage.

| Washery | Sample Code* | Ash+ (wt %) | Particle Size Disbtribution (wt %) | | | | |
|---|---|---|---|---|---|---|---|
| | | | 5-50 (mm) | 3-5 (mm) | 1-3 (mm) | 0.5-1 (mm) | <0.5 (mm) |
| Newcastle | F1 | 9.6 | — | 17.4 | 43.9 | 15.6 | 23.1 |
| Metropolitan | F2 | 12.1 | — | 1.8 | 26.4 | 22.0 | 49.8 |
| Stockton Borehole | F3 | 7.9 | — | 3.6 | 40.3 | 21.3 | 34.8 |
| AIS | F4 | 13.0 | — | 4.1 | 25.0 | 21.3 | 49.6 |
| Blend of F1-F4 | B1 | 10.1 | — | 11.7 | 31.5 | 21.5 | 35.3 |

*F: Crushed total product coal. B: blend. All are high-volatile A and medium-volatile bituminous (ASTM rank) coals from Broken Hill Proprietary Company Limited (BHP) Washeries. B1: blend of F1-F4 used as feed to BHP Newcastle coke ovens.
+Ash determined on air-dried basis.

Samples of known moisture content were prepared by thoroughly drying a ≈30 kg sample of each of the coals in Table 2 (in an air oven at 105° C.) and progressively adding sufficient water to obtain a known moisture in the range of 0-15 wt%. At each stage of moisture addition, the sample was mixed until completely homogeneous and replicate subsamples were taken for a moisture determination. The accuracy of the moisture determination by oven-drying was approximately ±0.1% moisture. The samples were packed into a wooden sample container (dimensions: 320 × 360 × 250 mm) to depths of approximately 50,100,150,200 and 250 mm for analysis. In the standard measurement geometry, the sample container was centrally positioned immediately above the dielectric filled transmitter horn. The mass per unit area (w) of each sample in the measurement path was calculated from the sample weight and the sample container dimensions. The phase shift and attenuation at each sample height and moisture content were calculated from the average of 100 measurements of the power at the outputs of the 8-port junction. The phase shift and attenuation of the empty sample container were substracted from these measurements to yield a phase shift and attenuation due to the sample alone. The attenuation was calculated from the measured incident ($P_i$), reflected ($P_r$) and transmitted ($P_t$) power using an equation of the form $$A = -10 \log_{10}(P_t/(P_i - P_r)) \quad (14)$$

The phase shift ($\phi$) and attenuation (A) were measured at 21 frequencies (0.05 GHz steps) in the range 2.8–3.8 GHz. For sample F1 the phase shift and attenuation were also determined at a frequency of 3.3 GHz. The measured A/W and $\phi$/W were correlated with oven-dried moisture (M) using a least squares fitting technique and equations of the form $$M = d_0 + d_1(\phi/W) + d_2(\phi/W)^2 \quad (15)$$

$$M = e_0 + e_1(A/W) \quad (16)$$

where $d_0, ..., e_1$ are fitting constants. The r.m.s. errors for correlations on single and multiple frequency measurements on sample F1 are presented in Table 3.

TABLE 3

R.m.s. errors for correlations of phase shift and attenuation against oven-dried moisture.

| Sample Code | Sample Thickness (mm) | Measurement Frequency (GHz) | R.m.s. Error (wt % moisture) | |
|---|---|---|---|---|
| | | | Attenuation (Equation (13)) | Phase Shift (Equation (12)) |
| F1 | 50–250 | 3.3 | 1.95 | 0.36 |
| | | 2.8–3.8* | 1.26 | 0.33 |

*21 measurements (0.05 GHz steps)

These results indicate there is a significant improvement in measurement accuracy when using multiple frequency measurements. The components of the r.m.s. error corresponding to the observed improvement in measurement accuracy are 1.49 and 0.14 wt % moisture for attenuation and phase shift respectively. The r.m.s. errors for multiple frequency measurements on samples F1–F4 and B1 are presented in Table 4. The mean r.m.s. errors for all samples are 0.37 and 1.14 wt % moisture for phase shift and attenuation respectively, indicating approximately a three times improvement in measurement accuracy when using a measurement of phase shift for the determination of moisture in coal.

TABLE 4

Correlation between gauge moisture and oven-dried moisture for samples B1 and F1–F4, at moisture contents in the range 0–15 wt %.

| Sample Code | No. of Data Points+ | R.m.s. Error (wt % moisture) | |
|---|---|---|---|
| | | Equation (12) | Equation (13) |
| F1 | 30 | 0.33 | 1.26 |
| F2 | 30 | 0.47 | 1.03 |
| F3 | 30 | 0.31 | 1.03 |
| F4 | 30 | 0.35 | 1.30 |
| B1 | 30 | 0.37 | 1.10 |

+Measurements at five heights at each of six moistures.

I claim:

1. An apparatus for the determination of the moisture content of a sample of varying thickness on a conveyor belt, said apparatus comprising:
   oscillator means to sequentially generate microwave signals at a plurality of discrete frequencies selected to compensate for frequency dependent cyclic variation in propagation characteristics within the sample;
   a first antenna, coupled to the oscillator means, located below said conveyor belt to direct said microwave signals through the sample;
   a second antenna disposed above said belt to receive the microwave signals transmitted through the sample;
   measurement means coupled to the second antenna and oscillator means for measuring the phase shift of the microwave signals transmitted through the sample; and
   computing means coupled to the oscillator means and to the measurement means for logging phase shifts of the respective received microwave signals with respect to the transmitted signals at each of said discrete frequencies and for calculating a moisture content of the sample from said phase shifts and a measure of mass per unit area of the sample.

2. An apparatus as claimed in claim 1 wherein said plurality of discrete frequencies are within a selected range of frequencies.

3. An apparatus as claimed in claim 2 wherein said plurality of discrete frequencies encompass substantially one period of the frequency dependent cyclic variations in propagation characteristics within said sample.

4. An apparatus as claimed in claim 2 wherein said plurality of discrete frequencies are equally spaced over said selected range.

5. An apparatus as claimed in claim 2 wherein said phase shifts of the respective signals are averaged to provide a single representative phase shift.

6. An apparatus as claimed in claim 1 including means to provide a measure of mass per unit area of the sample using measures of density and thickness.

7. An apparatus as claimed in claim 2 wherein said range of transmitted frequencies is within the frequency range of 2 to 4 GHz.

8. An apparatus as claimed in claim 1 wherein said number of discrete frequencies is greater than ten.

9. An apparatus as claimed in claim 6 wherein impedance matching material having a dielectric constant similar to that of the sample is interposed between the first antenna and the sample to reduce the interference of the transmitted signals with signals reflected from the sample.

10. An apparatus as claimed in claim 9 wherein the distance from the first antenna to the sample is substantially less than the wavelengths of the microwave signals.

11. A method for the determination of the moisture content of a sample of varying thickness on a conveyor belt, said method comprising the steps of sequentially transmitting through said sample microwave signals at a plurality of discrete frequencies selected to compensate for frequency dependent cyclic variation in propagation characteristics within said sample; determining the phase shifts of the respective received signals with respect to the transmitted signals at each of said discrete frequencies; and determining the moisture content of the sample from said phase shifts and a measurement of mass per unit area.

12. A method as claimed in claim 11 wherein said plurality of discrete frequencies are within a selected range of frequencies.

13. A method as claimed in claims 11 and 12 wherein said plurality of discrete frequencies encompass substantially one period of the frequency dependent cyclic variations in propagation characteristics within said sample.

14. A method as claimed in claim 12 wherein said plurality of discrete frequencies are equally spaced over said range.

15. A method as claimed in claim 13 wherein said phase shifts of the respective signals are averaged to provide a single representative phase shift.

16. A method as claimed in claim 12 wherein said range of transmitted frequencies is within the frequency range of 2 to 4 GHz.

17. A method as claimed in claim 16 wherein said number of discrete frequencies is greater than ten.

18. A method as claimed in claim 15 including the step of interposing between the first antenna and the sample an impedance matching material having a dielectric constant similar to that of the sample.

19. A method as claimed in claim 18 further including the step of positioning the first antenna at a distance from the sample which is substantially less than the wavelengths of the microwave signals.

20. A method as claimed in claim 11 wherein the mass per unit area of the sample is determined using a measurement of density and thickness.

* * * * *